United States Patent [19]

Tsao

[11] Patent Number: 5,084,018
[45] Date of Patent: Jan. 28, 1992

[54] SAFETY SYRINGE

[76] Inventor: Chien-Hua Tsao, No. 326, Pa-Te Rd., Sec. 2, Taipei, Taiwan

[21] Appl. No.: 691,812

[22] Filed: Apr. 26, 1991

Related U.S. Application Data

[63] Continuation-in-part of Ser. No. 393,390, Aug. 14, 1989, Pat. No. 5,019,044.

[51] Int. Cl.$^5$ ............................................. A61M 5/00
[52] U.S. Cl. .................................... 604/110; 604/195
[58] Field of Search ............... 604/195, 198, 187, 110, 604/218

[56] References Cited

U.S. PATENT DOCUMENTS

| | | | |
|---|---|---|---|
| 4,747,831 | 5/1988 | Kulli | 604/198 X |
| 4,838,863 | 6/1989 | Allard et al. | 604/195 X |
| 4,850,977 | 7/1989 | Bayess | 604/198 |
| 4,874,382 | 10/1989 | Lindemann et al. | 604/195 |
| 4,921,486 | 5/1990 | Dechellis et al. | 604/195 X |
| 4,978,343 | 12/1990 | Dysarz et al. | 604/195 |

Primary Examiner—John D. Yasko
Attorney, Agent, or Firm—Bacon & Thomas

[57] ABSTRACT

A safety syringe having a sliding base with a hole in a barrel to hold a locking tip to fix a needle cannula, in which the hole has a flange at the bottom to prevent downward sliding of the locking tip, the barrel being provided with a plurality of ventilation holes at the front end and a limiting flange at its inner wall to prevent from downward sliding of the sliding base so that the locking tip is positioned for injection, and a spring disposed at the locking tip between an end of the barrel and a needle extender so that when a hollow plunger with a cork at the top is pushed axially to the foremost position, the sliding base is forced to displace forwardly, and consequently the locking tip is forced to keep close contact with the extender and displace in an opposite direction. A further pushing of the plunger causes the fixed locking tip to pass through the flange at the bottom of the hole at the sliding base and then push the cork away from the plunger by upward displacement of the plunger. The cork, with the needle cannula and the locking tip, are displaced into the interior space of the plunger at the end of injection to prevent injury and infection from the used needle cannula.

3 Claims, 6 Drawing Sheets

SAFETY SYRINGE

CROSS-REFERENCE TO RELATED APPLICATION

This invention is a continuation-in-part of parent application Ser. No. 393,390, filed Aug. 14, 1989 now U.S. Pat. No. 5,019,044.

BACKGROUND OF THE INVENTION

The present invention relates to a safety syringe, particularly a simple syringe structure which can have its needle cannula retracted into its hollow plunger after injection to assure the safety of medical personnel and prevent reuse of the used syringe.

A conventional disposable syringe is made of plastic material and without indicating means to show whether it is brand new or used. A used syringe may be reused due to negligence or for lowering of operating costs, and consequently the patient who receives an injection with a used syringe may be infected by AIDS, hepatitis or other diseases transmitted through body fluid contact. Moreover, medical personnel who disposes of used syringes may be injured by a used needle cannula or infected with diseases from contact with the used needle cannula.

SUMMARY OF THE INVENTION

The main objective of the present invention is to provide an absolutely safe syringe with close contact between a sliding base and a plunger in a barrel to prevent medicine residues in the barrel after injection.

Another objective of the present invention is to provide a safety syringe with a simple structure to permit mass production of the syringe at the lowest possible cost.

DETAILED DESCRIPTION OF THE PREFERRED EMBODIMENTS

Figure 1:
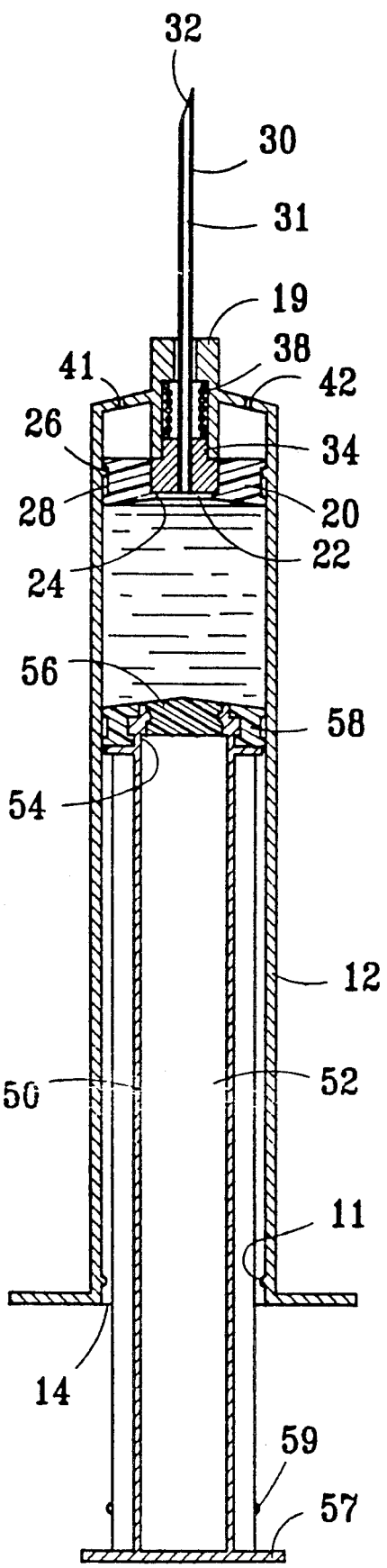
FIG. 1 is a sectional view of a safety syringe according to the present invention.
Figure 2:
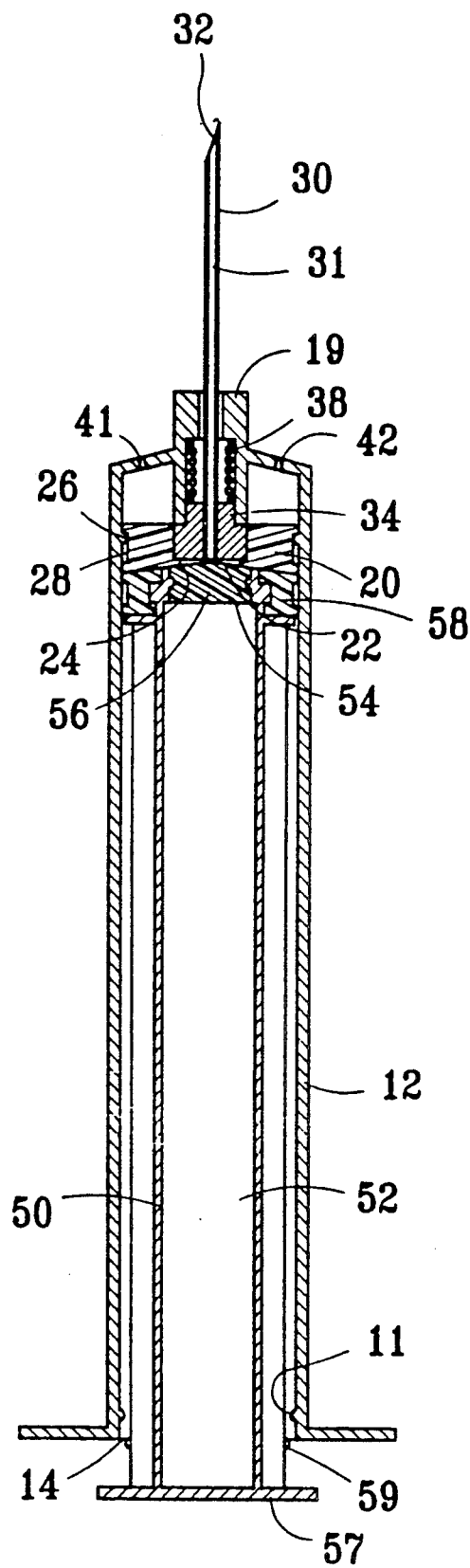
FIG. 2 is a sectional view of the safety syringe according to the present invention showing the syringe just before completion of an injection process.

Referring to FIGS. 1 and 2, a safety syringe (10), according to a first embodiment of the present invention, comprises a barrel (12) having a needle extender (19) at the front end. Two ventilation holes (41 and 42) are located besides the needle extender (19) at the end of the barrel (12). A needle cannula (30) is fixed to a locking tip (34) which is secured to a sliding base (20) having a round hole (22). The hole (22) has a flange (24) at the bottom to prevent the locking tip (34) from downward displacement. A limiting flange (26) is provided at an appropriate location on the inner wall of the front end of the barrel (12) to prevent the sliding base (20) from downward displacement so that the locking tip (34) and the sliding base (20) are positioned at a ready position. The sliding base (20) has a ring groove (28) at a lateral side to engage with the limiting flange (26) at the inner wall of the barrel (12) to prevent its downward displacement. A spring (38) extends through the locking tip (34) so that it is located between the barrel (12) and the needle extender (19) for a needle cannula (30) which has a passage (31) for medicine and a tip (32) for hypodermic injection through the passage (31).

Figure 3:
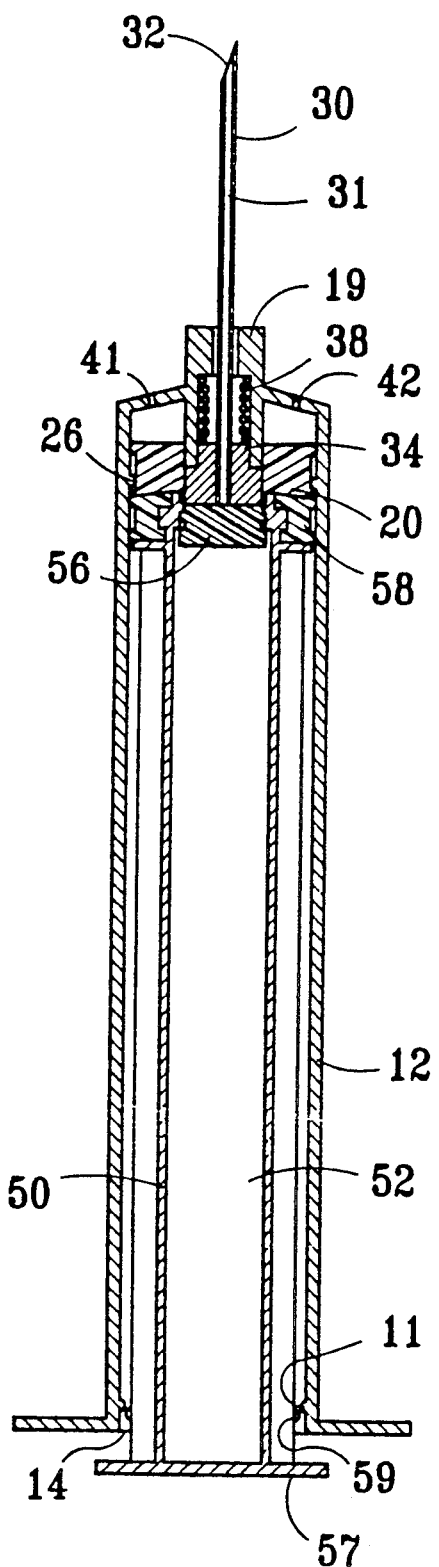
FIG. 3 is a sectional view of the safety syringe according to the present invention showing the locking tip being pushed by the plunger just before completion of an injection process.
Figure 4:
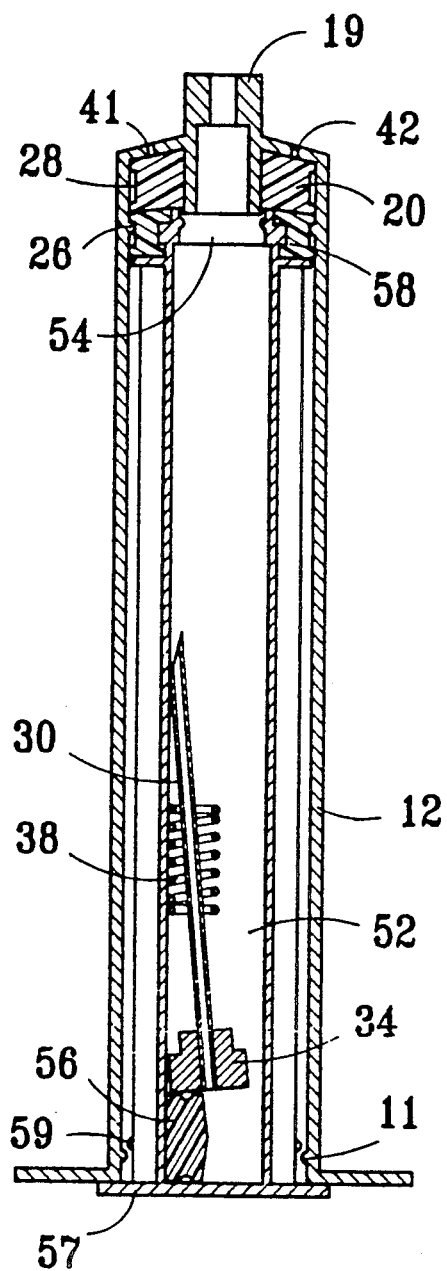
FIG. 4 is a sectional view of the safety syringe according to the present invention showing the disposition of the needle cannula within the interior space of the plunger.

Referring to FIGS. 3 and 4, the safety syringe (10) further includes a hollow plunger (50) made by high frequency molding or other appropriate method for axial displacement in the barrel. The plunger (50) is forcibly inserted into the barrel (12) from an open end (14) of the barrel (10), with the open end (14) of the barrel (10) being tightly sealed by a stopper (58). By the axial displacement of the plunger (50), medicine is drawn in to fill the barrel (12) by vacuum pressure, or expelled from the barrel (12) through the passage (31) at the needle cannula (30). The plunger (50) has a cork element (56) at its front end and seal the open end (14) of the barrel (12) to form a tightly closed space within the barrel (12). The cork element (56) is designed so that it can enter into the tightly closed space by operation of a thumb rest (57) provided at the other end of the plunger (50). Before each injection, the plunger (50) is pulled backwards to generate a vacuum pressure in the barrel (12) in order to draw medicine into the barrel (12) through the passage (31) at the needle cannula (30).

For injection, the tip (32) of the needle cannula (30) is first placed into a patient'skin and then the plunger (50) is pushed forward to inject the medicine from the barrel (12) through passage (31) into the patient's body. As soon as the plunger reaches its foremost position, the stopper (58) expels all the medicine out of the barrel (12), and maintains close contact with the bottom of the sliding base (20). When the plunger (50) is pushed further, the locking tip (34) is caused to push against the extender (19). Consequently, the extender (19) and the sliding base (20) are displaced in opposite directions. A further pushing of the plunger (50) causes the fixed locking tip (34) to pass through the flange (24) at the bottom of the hole (22) at the sliding base (20) by upward displacement of the plunger (50) during which the top of the plunger (50) continues to push the sliding base (20). By the upward pushing force from the plunger (50), the locking tip (34) reacts and push the cork (56) out of the open end (54) of the plunger (50). Then, the needle cannula (30) is only supported by the patient's muscle where the needle cannula (30) is pierced, the needle cannula (30) and the locking tip (34) are temporarily maintained at this injection position. After completion of the injection, as soon as the needle cannula (30) is pulled out of the patient's body, the needle cannula (30) and the locking tip (34) do not have any support, and hence they are brought into the internal space of the plunger (50) though the open end (54) formed by the displaced cork (56). The barrel (12) is designed with a plurality of ventilation holes (41 and 42) at the front end to facilitate injection.

The barrel (12) has a limiting flange (11) and the plunger (50) has a corresponding limiting flange (59). These limiting flanges (11 and 59) are designed to prevent the plunger (50) from backward displacement when it reaches the foremost position and to minimize space required for maintaining used syringe (10).

Figure 5:
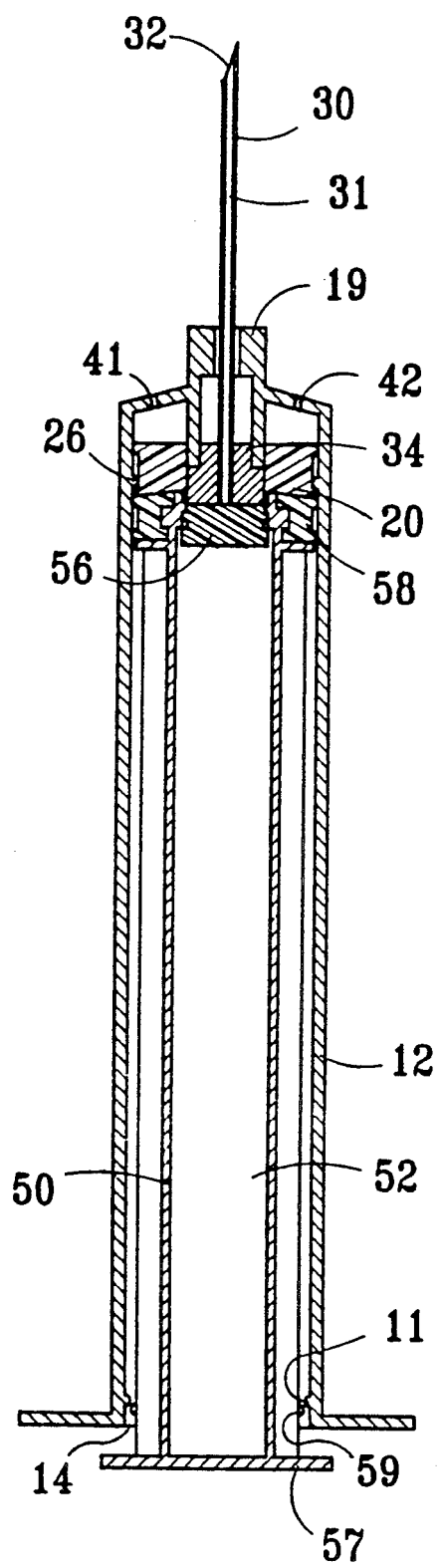
FIG. 5 illustrates the operation of the safety syringe without the spring according to the present invention.

Referring to FIG. 5, there is shown another embodiment of the present invention which does not have an element. It is mainly characterized by fixing of the locking tip (34) to the extender (19) at the top of the barrel (12) through the hole (22) at the sliding base (20) so that the syringe is ready for injection. As soon as the plunger (50) is pushed axially and reaches its foremost position, the sliding base (20) is pushed forwardly so that the fixed locking tip (34) and the sliding base (20) subjected to pushing by the plunger (50), are displaced in opposite directions. When the plunger (50) is pushed further, the sliding base (20) is compressed by the plunger (50) so that the bottom of the locking tip (34) is forced to pass through the flange (24) at the hole (22) of the sliding base (20), and engage the cork (56) at the foremost end of plunger (50). Consequently, the locking tip (34) and the cork (56) are displaced and fall into the interior space of the plunger (50).

Figure 6:
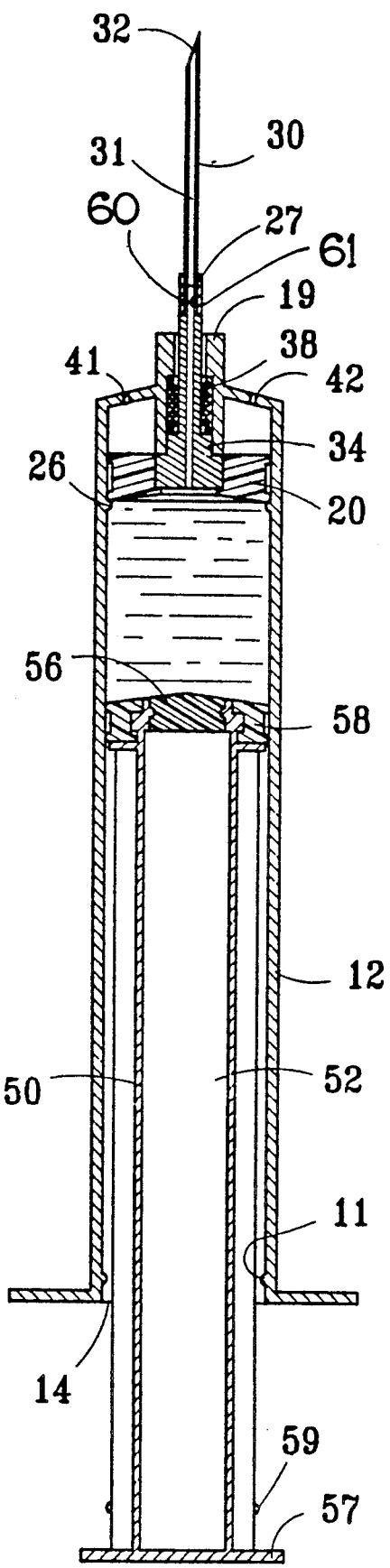
FIG. 6 is a sectional view of another embodiment of a safety syringe according to the present invention.

Referring to FIG. 6, there is shown another embodiment according to the present invention. The needle cannula (30) and the needle hub (27) used here are of conventional structure, and different types of needle cannula are available in the market for injection to different parts of the human body. The locking tip (34) is incorporated with an adapter (60) for fixing of the needle cannula (30) and the needle hub (27). The adapter (60) is designed with a passage (61) to connect the barrel (12) to the passage (31) of the needle cannula (30) for suction and injection of medicine. The retraction of the locking tip (34) with the adapter (60) carrying the needle hub (27) and the needle cannula (3) into the interior space of the plunger (50) are identical to that previously described and shown in FIGS. 1 through 5.

As clearly shown by the injection process illustrated by the drawings, the safety syringe according to the present invention has a simple structure with a plunger (50) for pushing a sliding base (20) into closing contact with a barrel's inner wall to the foremost position to minimize residual medicine in the barrel (12), and a needle cannula (30) having a locking tip (34) which are displayed into the interior space (42) of the plunger (50) by action of a spring (38) because there is no support for the needle cannula (30) and the locking tip after injection so that the needle cannula (30) will not be exposed to the environment. With such a structure, injury and infection by a used needle cannula can be prevented.

As indicated, the structure herein may be variously embodied. Recognizing various modifications will be apparent, the scope thereof shall be deemed to be defined by the claims as set forth below.

What is claimed is:

1. A safety syringe comprising:
a) a hollow barrel having an open back end and a front end, the front end being provided with a needle extender and a plurality of ventilation holes;
b) a locking tip disposed within the barrel and positioned adjacent the needle extender, and a needle cannula secured to the locking tip and extending outwardly through the needle extender;
c) a plunger having a front end, the plunger being slidably received in the barrel through the open back end and positioned in close contact with an inner wall of the barrel, the plunger including an opening at the front end communicating with an interior space therein, and a sealing element temporarily sealing the opening;
d) a sliding base having a hole therethrough, the locking tip being disposed within the hole, and a flange positioned at a bottom portion of the hole for securing the locking tip therein;
e) a limiting flange on the inner wall of the barrel and disposed in engagement with the sliding base to prevent the sliding base from moving away from the front end of the barrel; and
f) wherein when the plunger is axially slid towards the front end of the barrel, the front end of the plunger and sealing element engage the sliding base and locking tip to displace the sliding base and locking tip in opposite directions and also displace the sealing element, so that continued movement of the plunger towards the front end of the barrel causes the needle cannula, locking tip and sealing element to be disposed within the interior space of the plunger.

2. The safety syringe of claim 1 further including an elastic element positioned within the needle extender for urging the locking tip away from the front end of the barrel.

3. The safety syringe of claim 1 wherein the locking tip further includes an adapter extending outwardly of the needle extender for securing needle cannulae having different needle hubs.

* * * * *